United States Patent [19]

Muroi et al.

[11] 4,351,744
[45] Sep. 28, 1982

[54] KARL-FISCHER REAGENT

[75] Inventors: Kaname Muroi, Machida; Hiroko Fujino, Yamato, both of Japan

[73] Assignee: Mitsubishi Chemical Industries Limited, Tokyo, Japan

[21] Appl. No.: 192,880

[22] Filed: Oct. 1, 1980

[30] Foreign Application Priority Data

Oct. 31, 1979 [JP] Japan .................................. 54-140946

[51] Int. Cl.³ .......................................... G01N 33/18
[52] U.S. Cl. ................................... 252/408; 23/230 R
[58] Field of Search .......... 252/408; 23/230 R, 230 M

[56] References Cited

U.S. PATENT DOCUMENTS

| 2,780,601 | 2/1957 | Blomgren et al. | 252/408 |
| 2,967,155 | 1/1961 | Blomgren et al. | 252/408 |
| 3,656,907 | 4/1972 | Delmonte | 252/408 |
| 3,682,783 | 8/1972 | Dahms et al. | 252/408 |
| 3,749,659 | 7/1973 | Dahms et al. | 252/408 |
| 4,295,990 | 10/1981 | Verbeek et al. | 23/230 R |

FOREIGN PATENT DOCUMENTS 49-11599 3/1974 Japan .
55-15019 2/1980 Japan .
55-98350 7/1980 Japan .

OTHER PUBLICATIONS

Analytical Chemistry, vol. 27, No. 3, Mar. 1955, pp. 450–453, Peters, E. D. and Jungnickel, J. L.
Anylytica Chimica Acta, vol. 94 (1977), pp. 395–403, Verhoef, J. C. and Barendrechte, E.

Primary Examiner—Christine M. Nucker
Assistant Examiner—M. Moskowitz
Attorney, Agent, or Firm—Bierman & Bierman

[57] ABSTRACT

There is disclosed a Karl-Fischer reagent which consists essentially of iodide, sulfur dioxide, pyridine and an alkylene carbonate of the formula:

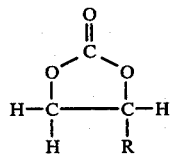

wherein R represents a hydrogen atom and a lower alkyl group. The reagent is superior in its high stability and a low iodine content.

7 Claims, No Drawings

KARL-FISCHER REAGENT

BACKGROUND OF THE INVENTION

1. Field of the Invention

This invention relates to a Karl-Fischer reagent the solvent of which is an alkylene carbonate.

2. Description of the Prior Art

Karl-Fischer reagent has been known and is a solution of iodine, sulfur dioxide and pyridine in an appropriate solvent. Various solvents of the Karl-Fischer reagent have been known. In view of stability of the reagent, chloroform is preferred (refer to Japanese Patent Publication No. 1748/58). A combination of chloroform with a small amount of a glycol gives more stable reagent (refer to Japanese Patent Publication No. 2598/63).

The inventors have conducted intensive studies to find a Karl-Fischer reagent having good stability using a solvent other than chloroform and have found that, with the use of an alkylene carbonate, a Karl-Fischer reagent of good stability can be prepared. Thus, this invention was developed on the basis of this knowledge.

SUMMARY OF THE INVENTION

Accordingly, an object of this invention is to provide a Karl-Fischer reagent having good stability.

Another object of this invention is to provide a Karl-Fischer reagent which is stable even though in the absence of chloroform.

A further object is to provide a Karl-Fischer reagent which has a low iodine content.

Therefore, in accordance with this invention there is provided a Karl-Fischer reagent consisting essentially of iodine, sulfur dioxide pyridine, and an alkylene carbonate of the formula:

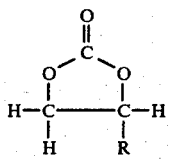

wherein R represents a hydrogen atom and a lower alkyl group.

DETAILED DESCRIPTION OF THE INVENTION

The Karl-Fischer reagent in accordance with this invention can be prepared according to any conventional procedure provided that the solvent is an alkylene carbonate.

It has already been known that a Karl-Fischer reagent reacts with water in a reaction medium of an alcohol, for example, methyl alcohol, in accordance with the following equations:

$$I_2 + SO_2 + 3C_5H_5N + H_2O \rightarrow 2C_5H_5N \cdot HI + C_5H_5N \cdot SO_3 \quad (1)$$

$$C_5H_5N \cdot SO_3 + CH_3OH \rightarrow C_5H_5N \cdot HSO_4CH_3 \quad (2)$$

Therefore, from the theoretical point of view, it is sufficient that the reagent contains one mole of sulfur dioxide and three moles of pyridine per iodine. However, in order to facilitate titration procedures, the reagent conveniently contains an excess of sulfur dioxide and pyridine, preferably more than 1.5 moles of sulfur dioxide and more than 5 moles of pyridine per iodine, because an excess of sulfur dioxide and pyridine accelerates the abovementioned reactions.

However, usually, from 2 to 10 moles of sulfur dioxide and from 6 to 30 moles of pyridine per iodine are conveniently employed. The reagent in accordance with this invention typically contains one mole of iodine, from 2 to 4 moles of sulfur dioxide and from 8 to 12 moles of pyridine. The Karl-Fischer reagent of this invention can be prepared by mixing iodine, sulfur dioxide and pyridine in the above proportion with an alkylene carbonate to obtain a solution. The amount of the alkylene carbonate is usually more than 100 ml, preferably more than 300 ml per liter of the reagent.

Example of the alkylene carbonate is a lower alkylene carbonate, for example, ethylene carbonate, propylene carbonate and butylene carbonate. The preferred carbonate is propylene carbonate. The carbonates are used alone or in combination as a solvent. The carbonate may be mixed with one or more other solvents, such as chloroform, but propylene carbonate is preferred. Ethylene carbonate which is a solid at room temperature is used as a solution in pyridine or other solvents. However, a large proportion of ethylene carbonate in the solution results in undesirable precipitation at low temperature.

The Karl-Fischer reagent of this invention is stable for a long time without addition of any stabilizer and the use of only the alkylene carbonate as the solvent is sufficient for this end where the strength is not more than 6 mg-$H_2O$/ml. The stability of the reagent can be further improved by removing all water from the components from which the reagent is prepared. When the reagent contains the alkylene carbonate alone as a solvent and has a strength as high as 10 mg-$H_2O$/ml, the stability is not so high. Such high strength reagent can be stabilized by addition of propylene glycol in an amount of about 1 to 3% by volume. With the addition of propylene glycol the strength lowers, but readjustment of the strength to a desired level can be accomplished by addition of more iodine.

As explained in the foregoing, the Karl-Fischer reagent containing an alkylene carbonate of this invention has various advantages; the lowering of the strength from the calculated level at the time of the preparation is small; it is stable for a long time; it can be readily prepared without heat generation; and a reagent having a strength which is close to the calculated level can be prepared by removing water as completely as possible from the components thereby reducing the amount of iodine. The Karl-Fischer reagent can be employed in determination of water content according to procedures similar to those employed in a conventional Karl-Fischer reagent which contains chloroform and which is available on the commercial market. During titration treatment, the reagent presents a brilliant yellow color, which changes to brown at the end of titration. This enables one to readily determine visually the end point.

Further, even though a reaction medium which does not contain an alcohol such as methyl alcohol is employed, the reaction of equation (1) above involving the Karl-Fischer reagent of this invention proceeds to an extent as high as 90 to 95%. This is suprising, because hitherto the presence of an alcohol was recognized to be essential for carrying out such reaction. Of course, the reaction of equation (1) above proceeds to completion in the presence of an alcohol, such as methyl alcohol. Therefore, in carrying out the Karl-Fischer method for determination of water content accurately, such alcohol must be present in the reaction medium.

This invention will be explained in further detail by means of the following examples. However, it should be noted that this invention is in no way limited by these examples in which the volumes of pyridine, propylene carbonate and the resulting solution are measured at room temperature, i.e., from about 20° to about 25° C.

EXAMPLE 1

Iodine, sulfur dioxide, pyridine and propylene carbonate in the amounts given in Table 1 were mixed to produce one liter of Karl-Fischer reagent.

No heat generation was observed during the mixing operation.

Twenty-five milliliters of methyl alcohol was placed in a titration flask and a Karl-Fischer reagent (Karl-Fischer reagent SS "MITSUBISHI" available from Mitsubishi Chemical Industries Limited, Tokyo, Japan) was added by titration to bring it to anhydrous state. Then, 5 ml of the reagent prepared as described above was added to the flask, the mixture was titrated with a Standard water in methanol solution to determine the strength of the reagent. The results are also given in Table 1.

TABLE 1

| Run No. | 1 | 2 | 3 |
|---|---|---|---|
| Iodine (g) | 17.1 | 49.6 | 84.8 |
| Sulfur dioxide (g) | 32.0 | 32.0 | 64.0 |
| Pyridine (ml) | 135 | 135 | 269 |
| Propylene carbonate (ml) | 835 | 835 | 670 |
| Strength (mg-$H_2O$/ml): | | | |
| Calculated | 1.21 | 3.51 | 6.01 |
| Found | 0.90 | 3.1 | 5.5 |

From the above, it was found that each reagent of this invention had a strength which is 0.5 mg-$H_2O$/ml or less below the calculated value. This difference is due to a trace amount of water present in the components and a trace amount of water absorbed inevitably from atmosphere during the preparation.

EXAMPLE 2

Iodine, sulfur dioxide, pyridine, ethylene carbonate and chloroform in the amounts given in Table 2 were mixed to prepare one liter of Karl-Fischer reagent. According to procedures similar to those of Example 1, the strength of the reagents was measured. The results are also given in Table 2.

TABLE 2

| Run No. | 4 | 5 |
|---|---|---|
| Iodine (g) | 42.4 | 84.7 |
| Sulfur dioxide (g) | 32.0 | 64.0 |
| Pyridine (ml) | 135 | 269 |
| Ethylene carbonate (ml) | 418 | 670 |
| Chloroform (ml) | 417 | — |
| Strength (mg-$H_2O$/ml): | | |
| Calculated | 3.00 | 6.00 |
| Found | 2.11 | 5.19 |

EXAMPLE 3

Iodine, sulfur dioxide, pyridine, propylene carbonate and chloroform in the amounts given in Table 3 were mixed to prepare 200 ml of Karl-Fischer reagent.

The strength of the reagents was determined according to procedures similar to those of Example 1. The results are given in Table 3.

TABLE 3

| Run No. | 6 | 7 | 8 |
|---|---|---|---|
| Iodine (g) | 16.9 | 16.9 | 16.9 |
| Sulfur dioxide (g) | 12.8 | 12.8 | 12.8 |
| Pyridine (ml) | 54 | 54 | 54 |
| Propylene carbonate (ml) | 68 | 45 | 24 |
| Chloroform (ml) | 66 | 89 | 110 |
| Strength (mg-$H_2O$/ml): | | | |
| Calculated | 5.99 | 5.99 | 5.99 |
| Found | 5.27 | 5.32 | 5.41 |

EXAMPLE 4

Iodine (8.45 g), sulfur dioxide (4.95 g), pyridine (26.7 ml), propylene carbonate (12 ml) and ethylene carbonate (55 ml) were mixed to prepare 100 ml of Karl-Fischer reagent. The strength was found to be 5.25 mg-$H_2O$/ml (calculated being 5.99 mg-$H_2O$/ml).

EXAMPLE 5

One liter of Karl-Fischer reagent was prepared by mixing 42.4 g of iodine and 89 ml of a solution of pyridine and sulfur dioxide (molar ratio being 10:6), 68 ml of pyridine and 835 ml of propylene carbonate. The calculated strength was 3.00 mg-$H_2O$/ml.

The reagent was stored in an air-tightly sealed brown reagent bottle maintained at room temperature. A portion of the reagent was taken out from the bottle at intervals and the strength was measured. The results are given in Table 4.

TABLE 4

| Storage (day) | Strength (mg-$H_2O$/ml) |
|---|---|
| 0 | 2.25 |
| 25 | 2.17 |
| 37 | 2.19 |
| 84 | 2.18 |
| 115 | 2.18 |
| 120 | 2.17 |
| 187 | 2.07 |
| 279 | 2.02 |

Each component employed in preparing the reagent contained a trace amount of water and absorbed a trace amount of water from the atmosphere during the preparation. Therefore, the reagent has a strength lower than the calculated value. The strength decreases as time elapses, due to a trace amount of water present at the time of preparation and a trace amount of water absorbed when the reagent is taken out from the bottle. Therefore, it is expected that, if precautions are taken to prevent intake of water, no substantial decrease in the strength will be observed.

We claim:

1. In a Karl-Fischer reagent which consists essentially of iodine, sulfur dioxide, pyridine and a solvent, the improvement wherein the solvent comprises an alkylene carbonate of the formula:

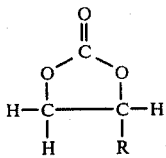

wherein R represents a hydrogen atom or a lower alkyl group.

2. A Karl-Fischer reagent in accordance with claim 1, wherein the solvent consists essentially of an alkylene carbonate.

3. A Karl-Fischer reagent in accordance with claim 1, wherein the solvent consists essentially of an alkylene carbonate and chloroform.

4. A Karl-Fischer reagent in accordance with claim 1, wherein said alkylene carbonate is propylene carbonate.

5. A Karl-Fischer reagent in accordance with claim 1, wherein the proportions of sulfur dioxide and pyridine are more than 1.5 moles and more than 5 moles per iodine, respectively.

6. A Karl-Fischer reagent in accordance with claim 1, wherein the proportion of said alkylene carbonate is more than 10% by volume.

7. A Karl-Fischer reagent in accordance with claim 1, wherein the proportion of said alkylene carbonate is more than 30% by volume.

* * * * *